United States Patent [19]

Nakano et al.

[11] Patent Number: 5,132,377

[45] Date of Patent: Jul. 21, 1992

[54] HEAT-LATENT, CATIONIC POLYMERIZATION INITIATOR AND RESIN COMPOSITIONS CONTAINING THE SAME

[75] Inventors: Shinji Nakano, Takatsuki; Satoshi Urano, Tanabecho, both of Japan

[73] Assignee: Nippon Paint Company, Limited, Osaka, Japan

[21] Appl. No.: 532,716

[22] Filed: Jun. 4, 1990

[30] Foreign Application Priority Data

Jun. 5, 1989 [JP] Japan .................................. 1-142541
Jul. 24, 1989 [JP] Japan .................................. 1-191659
Sep. 19, 1989 [JP] Japan .................................. 1-244681

[51] Int. Cl.$^5$ .................... C08F 288/04; C08F 29/02; C08F 20/00; C08F 8/32
[52] U.S. Cl. .................................... 525/509; 525/162; 525/443; 525/519; 525/474; 525/375; 525/379; 528/244; 528/224; 528/217; 528/355; 528/408; 528/424
[58] Field of Search .............. 525/509, 162, 443, 519, 525/474, 375, 379; 528/355, 408, 424; 526/204, 220, 217

[56] References Cited

PUBLICATIONS

Thermoinitiated Cationic Polymerization of Styrene with a Pyridinium Salt, Uno Hitomi, Chem. Lett. Feb. 1988 (pp. 935–938).
Macromolecules 1990, 23, 431–434 publication date: Jan. 22, 1990.

*Primary Examiner*—James J. Seidleck
*Assistant Examiner*—W. R. H. Clark
*Attorney, Agent, or Firm*—Millen, White & Zelano

[57] ABSTRACT

Quaternary ammonium salts of a non-nucleophilic anion having an α-substituted benzyl group attached to the quaternary nitrogen atom or having a heterocycle including the quaternary nitrogen atom are useful as a cation polymerization initiator having a heat latency. A variety of resinous compositions containing this initiator is also disclosed.

4 Claims, No Drawings

HEAT-LATENT, CATIONIC POLYMERIZATION INITIATOR AND RESIN COMPOSITIONS CONTAINING THE SAME

BACKGROUND OF THE INVENTION

This invention relates to a novel class of cationic polymerization initiators having a heat-latency, i.e. which are normally inactive but are capable of initiating a cationic polymerization reaction only at an elevated temperature. The invention also relates to heat-curable resin compositions containing these initiators which are useful for the preparation of coating, adhesive, printing ink and other compositions.

A variety of cationic polymerization initiators are known including Friedel-Crafts catalysts such as aluminum chloride, boron trifluoride-ether complex, photodegradable onion salts (S, Se, Te), diallyl iodonium salts and the like. These known initiators are generally not selective with respect to the reactioin temperature. Therefore, an epoxy resin containing these initiators begins to cure even at room temperature.

Japanese Laid Open Patent Application (Kokai) Nos. 37003/83 and 37004/83 disclose another type of cationic polymerization initiators. They are aliphatic or aromatic sulfonium salts capable of generating carbonium cations upon heating to an elevated temperature. Initiators of this type are known as "heat-latent cationic polymerization initiator". Cation-polymerizable resins such as epoxy resins containing the heat-latent initiator are, therefore, normally inactive but capable of curing at a temperature above the cleaving temperature of the initiator. This provides a heat-curable, one-component epoxy resin composion having a greater storage-stability and a longer pot life.

The carbonium cations produced by the thermal cleavage of the heat-latent initiator may react with water or a hydroxy group-containing compound to generate protons which, in turn, catalyze various cross-linking reactions. Accordingly, the heat-latent cationic initiator may find uses in catalyzing the curing reaction of, for example, polyester and acrylic resins with melamine resins. This also provides systems having a greater storage stability.

The heat latent cationic initiator thus has a number of advantages over conventional cationic initiators or proton-donating catalysts. Unfortunately, the prior art sulfonium type initiators have a serious problem in that their sulfur-containing decomposition products are malodorous. This limits their uses in practice.

Accordingly, a strong need exists for a heat latent cationic polymerization initiator which obviates the above defects.

SUMMARY OF THE INVENTION

In one aspect, the present invention provides a compound of the formula:

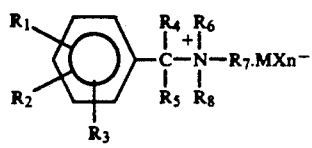

wherein $R_1$, $R_2$ and $R_3$ are each hydrogen, halogen, alkyl, alkoxy, nitro, amino, alkylamino, cyano, alkoxycarbonyl or carbamoyl; $R_4$ is hydrogen, halogen or alkyl; $R_5$ is halogen or alkyl; $R_6$, $R_7$ and $R_8$ are each alkyl or alkenyl optionally substituted with hydroxy, carboxyl, alkoxy, nitro, cyano or alkanoyloxy, or phenyl optinally substituted with alkyl, halogen, nitro, cyano, alkoxy, amino or dialkylamino; M is As, Sb, B or P; X is halogen; and n equals to the valency of the element M plus one;

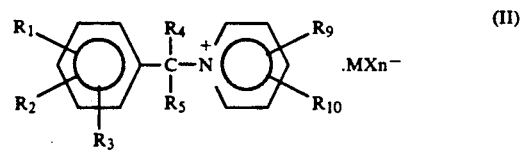

where $R_1$, $R_2$, $R_3$, $R_4$, $R_5$ M, X and n are as defined above with proviso that $R_4$ cannot represent hydrogen; $R_9$ and $R_{10}$ are each hydrogen, alkyl, halogen, nitro, cyano, alkoxy, amino or dialkylamino; or

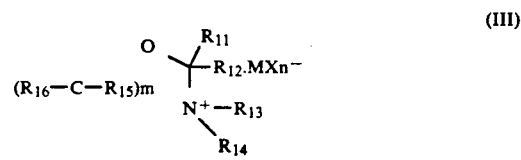

wherein M, X and n are as defined above; $R_{11}$ and $R_{12}$ are each hydrogen, alkyl, alkenyl or phenyl optionally substituted with hydroxy, alkyl, alkoxy, halogen, nitro, cyano or alkylamino; $R_{13}$ and $R_{14}$ are each alkyl, alkenyl or phenyl optionally substituted with hydroxy, alkyl, alkoxy, halogen, nitro, cyano or alkylamino; $R_{15}$ and $R_{16}$ are each hydrogen, hydroxy, alkyl, alkoxy or phenyl optionally substituted with hydroxy, alkyl, alkoxy, halogen, nitro, cyano or alkylamino; and m is an integer of 1-4.

In another aspect, the present invention provides a heat-curable resin composition comprising an amount of the above compound I, II or III effective to initiate the curing reaction of the composition at an elevated temperature.

The above compound I, II or III may be utilized in any one of the following systems:

I. Systems solely containing a cation polymerizable monomer, polymer or a mixture thereof as a heat-curable component;

II. Systems containing a cation-polymerizable monomer, polymer or a mixture thereof and a polyol;

II. Systems containing a film-forming, hydroxy group-containing resin and a melamine resin;

IV. Systems capable of curing through a self-condensation reaction of an alkoxysilyl group-containing resin; and V. Systems capable of curing through a co-condensation reaction of an alkoxysilyl group-containing resin and a hydroxy group-containing resin.

DETAILED DISCUSSION

1. Heat-Latent Cationic Initiator

The compound of the formula I:

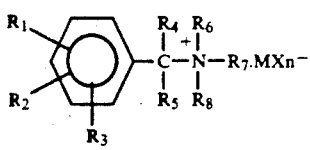 (I)

may be synthesized by reacting a correspondining α-substituted benzyl halide of the formula IV:

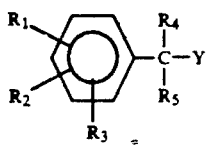 (IV)

where Y is halogen, with a tertiary amine of the formula V:

 (V)

and then reacting the resulting ammonium halide with an alkali metal salt of the complex anion $MXn^-$ to metathetically produce the compound I.

Similarly, the compound of the formula II:

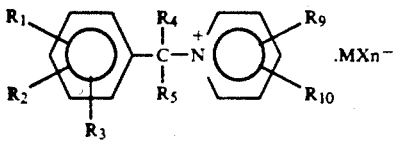 (II)

may be synthesized by reacting the α-substituted benzyl halide (IV) with a pyridine of the formula (VI):

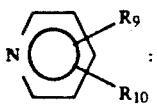 (VI)

and then reacting the resulting pyridinium halide with an alkali metal salt of the complex anion $MXn^-$.

The compounds of the formula I or II are thermally cleaved at an elevated temperature to produce a benzyl cation of the formula:

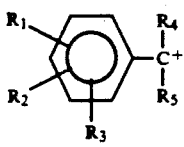

which, in turn, initiates a cationic polymerization chain reaction. However, these compounds are substantially inactive at a temperature below their cleaving points. Therefore, they find a number of valuable uses such as a hardener of one-component epoxy resins.

The compound of the formula III:

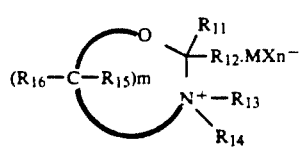 (III)

may be synthesized by reacting an aminoalkanol of the formula (VII):

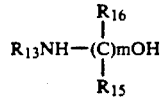 (VII)

with an aldehyde or ketone of the formula: $R_{11}COR_{12}$ to produce a compound of the formula (VIII):

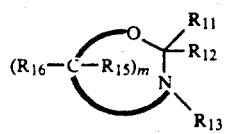 (VIII)

quaternizing the compound VIII with a halide of the formula $R_{14}$-hal to produce an ammonium halide of the formula IX:

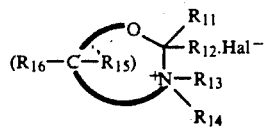 (IX)

and then exchanging the halide anion of the ammonium halide IX with the complex anion $MXn^-$.

The compound of the formula III is thermally decomposed to release an acid HMXn capable of initiating the cation polymerization reaction according to the following reaction sheme:

(III) 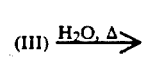

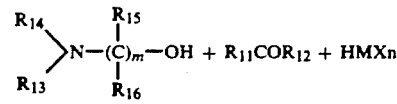

Therefore, the compound III is useful as a heat-latent cation polymerization initiator as well.

2. Heat-Curable Resin Compositions

I. Cation-polymerizable systems

Typical examples of cation-polymerizable monomers are those having a cation-polymerizable functional group such as epoxide, cyclic imine, cyclic ether, cyclic ester, and other groups.

For use as a vehicle for coating compositions, adhesives, printing inks and the like, the resin composition may comprise a cation-polymerizable oligomer and/or polymer including the same structure as the above cation-polymerizable monomer in their molecules. The resin composition may be of the solventless type containing the above-mentioned cation-polymerizable monomer and/or a low molecular weight-polyol as a reactive diluent, or it may contain a conventional organic solvent for adjusting its viscosity to a suitable range for application.

Typical examples of cation-polymerizable resins are epoxy resins including bisphenol A-, bisphenol S- and bisphenol F epoxy resins; novolac type epoxy resins; diglycidyl ethers of glycols such as butanediol, hexanediol and hydrogenated bisphenol A; diglycidyl ethers of polyoxyalkylene glycols such as polyethylene glycol, polypropylene glycol and bisphenol A-alkylene oxide adducts; diglycidyl esters of dicarboxylic acids such as terephthalic acid, isophthalic acid, phthalic acid and adipic acid; and glycidyl ether-esters of hydroxycaboxylic acids such as p- and m-hydroxybenzoic acids.

Also included in examples of preferred cation-polymerizable resins are epoxide group-containing acrylic resins. These acrylic resins are produced by polymerizing a monomer mixture of glycidyl (methy)acrylate with a (meth)acrylic acid ester such as methyl (meth)acrylate, butyl (meth)acrylate, isobutyl (meth)acrylate and 2-hydroxyethyl (meth)acrylate optionally containing other comonomers such as styrene or its derivatives, acrylonitrile, vinyl acetate and the like.

Examples of usable polyols include low molecular weight-polyols such as ethylene glycol, propylene glycol, tetramethylene glycol, diethylene glycol, glycerine, trimethylolpropane and pentaerythritol. It should be noted that these low molecular weight-polyols produce $H^+$ through a chain transfer reaction causing unwanted reactions of cation-polymerizable functional groups. This often results in a cured resin having a low average molecure weight and thus poor mechanical properties. Accordingly, it is more preferable to use an oligomer polyol such as polyether polyols, polycaprolactone polyol, polyester polyols and acryl polyols.

These polyols may be added to the resin composition in such an amount that their hydroxy function is 1 to 100 mole percent relative to the cation-polymerizable functional group. If the amount of polyol is too low, it is difficult to adjust the workability of the resulting composition in a suitable range and the composition is not high solids. Conversely, excessive use of polyls adversely affects the curability of the entire composition.

The composition of this invention contains from 0.01 to 10%, preferably from 0.05 to 5% by weight of the resin solid content of the initiator compound of the formula I, II or III. If the amount of the initiator is deficient, the curability of the composition is not satisfactory. Conversely, excessive use of the initiator adversely affects the physical properties of cured composition, such as dark appearance and decreased water resistance.

The composition may contain conventional additives such as pigments, fillers and the like depending upon its intended use.

The resulting composition may be provided as the high solids or solventless type and has an increased storage stability at room temperature although curable at a temperature above the cleaving point of the initiator.

II. Systems containing melamine resins

Melamine resin-containing coating compositions or enamels are well-known in the art.

These compositions usually contain a proton-donor such as p-toluenesulfonic acid for catalyzing the cross-linking reaction with the melamine resin. Since the addition of a free acid to the composition tends to cause gelling of the entire composition upon storage, the catalyst is blocked partially or totally in its acid catalyst is blocked partially or volatile at the curing temperature of the composition. However, the curability of this type of compositions is generally not compatible with the storage stability thereof.

The use of the cationic polymerization initiator of the present invention overcomes this problem. The initiator is substantially inactive until a critical temperature is reached. However, a proton is generated from the initiator by heating the initiator in the presence of water or a hydroxy group-containing compound contained in the composition. This enables for the curability and storage stability of the composition to be compatible.

Various film-forming resins are used in the coating industry in combination with a melamine resin. Examples thereof include polyester resins, polylactone resins, epoxy resins, acrylic resins and the like.

Polyester resins are prepared by the condensation reacation of a polycarboxylic acid or its anhydride with a polyhydric alcohol. Any polyester resin havinig a hydroxy function at the terminal and/or middle of the polyester chain may be cross-linked with the melamine resin.

Hydroxy terminated polyactone resins may also be cross-linked with the melamine resin.

Epoxy resins having an epoxide function and a hydroxy function at the terminal and the middle of the molecule respectively such as bisphenol epoxy resins and novolac epoxy resins may be used in combination with the melamine resin.

Acrylic resins containing a plurality of hydroxy functions may be prepared by copolymerizing a hydroxy group-containing acrylic monomer such as 2-hydroxyethyl (meth)acrylate with one or more comonomers such as alkyl (meth)acrylates, e.g. methyl (meth)acrylate, butyl (meth)acrylate, isobutyl (meth)acrylate and 2-ethylhexyl (meth)acrylate; styrene or its derivatives; (meth)acrylonitrile; vinyl acetate and the like.

Melamine resins are prepared by reacting a triazine compound such as melamine, acetoquanamine or benzoguanamine with formaldehyde, and optionally etherifying the methylol function of the resulting condensate partially or totally with a lower alkanol such as methanol or butanol.

Thermosetting resin compositions comprising a hydroxy group-containing, film-forming resin and a melamine resin are well-known in the coating industry. Except for the use of the above-discussed cationic polymerization initiator, the composition of the present invention may be otherwise identical to these known compositions.

The weight ratio of the hydroxy group-containing, film-forming resin to the melamine resin ranges between 50:50 to 95:5 on the solid content basis.

The composition of this invention contains from 0.01 to 10%, preferably from 0.05 to 5% by weight of the resin solid content of the initiator of the formula I, II or III. If the amount of the initiator is deficient, the curability of the composition is not satisfactory. Conversely, excessive use of the initiator adversely affects the physical properties of cured composition such as dark appearance and decreased water resistance.

The composition may contain convenational additives such as pigments, fillers and the like depending upon its intended use.

III. Systems utilizing the self-condensation or co-condensation reaction of alkoxysilyl groups Japanese Patent Publication No. 33512/88 discloses a curable resin composition containing a vinyl polymer having a plurality of alkoxysilyl group-containing side chains, a polyhydroxy compound and a curing catalyst. It is believed that the composition cures through a self-condensation reaction between two alkoxysilyl groups:

ROSi—+—SiOR+H₂O→—Si—O—Si—+2ROH as well as a co-condensation reaction of an alkoxysilyl group and a hydroxy group:

ROSi—+HO—C—→—Si—O—C—+ROH

A variety of catalysts are disclosed as being capable of catalyzing the above reactions. These include amines such as butylamine, dibutylamine, t-butylamine, ethylenediamine and the like; organic metal compounds such as tetraisopropyl titanate, tetrabutyl titanate, tin octate, lead octate, zinc octate, calcium octate, dibutyltin diacetate, dibutyltin dioctate, dibutyltin dilaurate and the like; and acid catalysts such as p-toluenesulfonic acid, trichloroacetic acid and the like. The composition containing these catalysts is curable at room temperature. As is self-explanatory from this fact, the composition cannot be stored for a long period of time while containing the curing catalyst. When long term storage is desired, it is necessary to store the catalyst and the resin component separately and mix the two components immediately prior to use. This is inconvenient in practice and requires to use within a pot life. Other approach includes to reduce the amount of catalyst and blocking the amine or acid catalyst with a suitable acid or amine. Unfortunately they all have been proven unsatisfactory in terms of film properties, storage stabilities and the like.

Similar to the melamine resin-containing composition, the use of the cationic polymerization initiator of the present invention in the above-mentioned system overcomes these problems.

Examples of film-forming resins containing a plurality of alkoxysilyl groups include the following:

(1) Acrylic resins containing alkoxysilyl groups

A monomer having both an ethylenically unsaturated function and an alkoxysilyl function in the molecule forms a homopolymer or copolymer containing a plurality of alkoxysilyl groups by itself or with acrylic and/or other comonomers.

A first class of such monomers are alkoxysilylalkyl esters of acrylic or methacrylic acid of the formula:

$$CH_2=\overset{R}{\underset{|}{C}}-COO(CH_2)_xSi(R')_y(OR'')_{3-y}$$

wherein R is H or CH₃, R' and R" are each alkyl, x is an integer, and y is 0, 1 or 2.

Specific examples of these monomers include
γ-methacryloyloxypropyltrimethoxysilane,
γ-methacryloyloxypropylmethyldimethoxysilane,
γ-methacryloyloxypropyldimethylmethoxysilane,
γ-methacryloyloxypropyltriethoxysilane,
γ-methacryloyloxypropylmethyldiethoxysilane,
γ-methacryloyloxypropyldimethylethoxysilane,
γ-methacryloyloxypropyltripropoxysilane,
γ-methacryloyloxypropylmethyldipropoxysilane,
γ-methacryloyloxypropyldimethylpropoxysilane,
γ-methacryloyloxypropyltributoxysilane,
γ-methacryloyloxypropylmethyldibutoxysilane, and
γ-methacryloyloxypropyldimethylbutoxysilane.

A second class of said monomers are adducts of (meth)acrylic acid with an epoxy group-containing alkoxysilane such as
β-glycidylpropyltrimethoxysilane or
β-(3,4-epoxycyclohexyl)ethyltrimethoxysilane.

Another class of alkoxysilyl group-containing monomers are adducts of a hydroxyalkyl (meth)acrylate such as hydroxyethyl (meth)acrylate, hydroxypropyl (meth)acrylate or 4-hydroxybutyl (meth)acrylate with an isocyanotoalkylalkoxysilane of the formula:

$$OCN(CH_2)_xSi(R')_y(QR'')_{3-y}$$

such as
γ-isocyanatopropyltrimethoxysilane,
γ-isocyanatopropylmethylmethoxysilane,
γ-isocyanatopropyltriethoxysilane or
γ-isocyanatopropylmethyldiethoxysilane.

A further class of alkoxysilyl group-containing monmers are adducts of glycidyl (meth)acrylate with an aminoalkylalkoxysilane such as
γ-aminopropyltrimethoxysilane,
γ-aminopropyltriethoxysilane,
3-(2-aminoethylamino)propylmethyldimethoxysilane,
3-(2-aminoethylamino)propyltrimethoxysilane,
γ-aminopropyldimethylmethoxysilane or
γ-aminopropylmethyldimethoxysilane.

Acrylic and/or other comonomers which may be copolymerized with the alkoxysilyl group-containing monomer include alkyl (meth)acrylates, (meth)acrylic acid, (meth)acrylonitrile, (meth)arylamide, styrene, vinyl chloride, vinyl acetate and the like.

(2) Silicon-modified epoxy resins

The above-mentioned aminoalkylalkoxysilanes used for preparing an adduct with glycidyl (meth)acrylate may be reacted with an epoxy resin to produce a modified epoxy resin having a plurality of alkoxysilyl groups.

(3) Silicon-modified polyester resins

Polyester resins having a plurality of free carboxyl groups may be modified with the above-mentioned epoxy group-containing alkoxysilane to give silicon-modified polyester resins.

Polyesters having a plurality of hydroxy groups may be reacted with the above-mentioned isocyanatoalkylalkoxysilane to give silicone-modified polyester resins.

Typical examples of hydroxy group-containing resins include polyester resins, polyactone resins, epoxy resins and acrylic resins.

Polyester resins are prepared by the condensation reaction of a polycarboxylic acid or its anhydride with a polyhydric alcohol. Any polyester resin having a hydroxy function at the terminal and/or middle of the polyester chain may be employed.

Hydroxy terminated polyactone resins may also be employed.

Epoxy resins having an epoxide function and a hydroxy function at the terminal an the middle of the molecule respectively, such as bisphenol epoxy resins and novolac epoxy resins may be employed.

Acrylic resins containing a plurality of hydroxy functions may be prepared by copolymerizing a hydroxy group-containing acrylic monomer such as 2-hydroxyethyl (meth)acrylate with one or more comonomers such as alky (meth)acrylates, e.g. methyl (meth)acrylate, butyl (meth)acrylate, isobutyl (meth)acrylate and 2-ethylhexyl (meth)acrylate, styrene or its derivatives; (meth)acrylonitrile, vinyl acetate and the like.

Systems utilizing the self-condensation reaction of alkoxysilyl groups contain the above-mentioned silicon-containing resin and from 0.01 to 10%, preferably from 0.05 to 5% by weight of the resin solid content of the compound I, II or III.

Systems utilizing the co-condensation of alkoxysilyl group with hydroxy group contain the above-mentioned silicon-containing resin, an amount of hydroxy group-containing resin at a molar ratio of the hydroxy group per alkoxysilyl group of 0.1 to 10, and from 0.01 to 10%, preferably from 0.05 to 5% by weight of the resin solid content of the compound I, II or III.

If the amount of compound I, II or III is deficient, the curability of the composition is not satisfactory. Conversely, excessive addition of the compound I, II or III adversely affets the physical properties of cured composition such as dark appearance and decreased water resistance.

The composition may contain conventional additives such as fillers, pigments and the like depending upon its intended use.

The resulting composition has an increased storage stability at room temperature but curable at a temperature above the cleaving point of the compound I, II or III. The curing time may vary with the curing temperature but usually within one hour.

The following examples are intended to further illustrate the present invention without limiting thereto. All parts and percents therein are by weight unless otherwise indicated.

EXAMPLES

Part I. Synthesis of Initiators

Example I-1

N-$\alpha$-methylbenzyl-N,N-dimethylanilinium hexafluoroantimonate 4.218 g (0.03 mol) of $\alpha$-methylbenzyl chloride and 3.638 g (0.03 mol) of N,N-dimethylaniline were reacted in 40 ml of methanol at 40° C. for 3 days. After the reaction, the solvent was evaporated in vacuo and ether-water was added to the residue to extract unreacted reactants in the etherial layer. To the aqueous layer was added 7.77 g (0.03 mol) of sodium hexafluoroantimonate. The resulting crystals were suction filtered, washed and dried to give the title compound.

NMR: 1.7 ppm (d, 3H, Me), 3.6 ppm (s, 6H, Me), 4.8–4.9 ppm (q, 1H, CH), 7.1–7.6 ppm (m, 10H, Ph)

Examples I-2 to I-15

Analogous to Example I-1, the following compounds were synthesized.

(2) N-2-hydroxyethyl-N-$\alpha$-methylbenzyl-N,N-dimethylammonium hexafluoroantimonate;

NMR: 1.7 ppm (d, 3H, Me), 3.1 ppm (s, 6H, Me), 3.3–3.4 ppm (t, 2H, CH$_2$), 3.9 ppm (t, 2H, CH$_2$), 4.8 ppm (q, 1H, CH), 7.5–7.6 ppm (m, 5H, Ph);

(3) N-$\alpha$-methylbenzyl-N,N,N-trimethylammonium hexafluoroantimonate,

NMR: 1.7 ppm (d, 3H, Me), 3.1 ppm (s, 9H, Me), 4.8 ppm (q, 1H, CH), 7.5–7.6 ppm (m, 5H, Ph);

(4) N-2-hydroxyethyl-N-p-chloro-$\alpha$-methylbenzyl-N,N-dimethylammonium hexafluoroantimonate;

NMR: 1.7 ppm (d, 3H, Me), 3.1 ppm (s, 6H, Me), 3.3–3.4 ppm (t, 2H, CH$_2$), 3.9 ppm (t, 2H, CH$_2$), 4.8 ppm (q, 1H, CH), 7.5–7.6 ppm (m, 4H, Ph)

(5) N-p-methyl-$\alpha$-methylbenzyl-N,N,N-trimethylammonium hexafluoroantimonate, NMR: 1.7 ppm (d, 3H, Me), 2.3 ppm (s, 3H, Me), 3.1 ppm (s, 9H, Me), 4.8 ppm (q, 1H, CH), 7.5–7.6 ppm (m, 4H, Ph);

(6) N-$\alpha$-methylbenzyl-N,N,N-trimethylammonium hexafluorophosphate,

NMR: 1.7 ppm (d, 3H, Me), 3.1 ppm (s, 9H, Me), 4.8 ppm (q, 1H, CH), 7.5–7.6 ppm (m, 5H, Ph);

(7) N-2-hydroxyethyl-N-p-chloro-$\alpha$-methylbenzyl-N,N-dimethylammonium tetrafluoroborate, NMR: 1.7 ppm (d, 3H, Me), 3.1 ppm (s, 6H, Me), 3.3–3.4 ppm (t, 2H, CH$_2$), 3.9 ppm (t, 2H, CH$_2$), 4.8 ppm (q, 1H, CH9, 7.5–7.6 ppm (m, 4H, Ph);

(8) N-$\alpha,\alpha$-dimethylbenzyl-N,N-dimethylanilinium hexafluoroantimonate, NMR: 1.7 ppm (s, 6H, Me), 3.6 ppm (s, 6H, Me), 7.1–7.6 ppm (m, 10H, Ph);

(9) N-2-hydroxyethyl-N-$\alpha,\alpha$-dimethylbenzyl-N,N-dimethylammonium hexafluoroantimonate, NMR: 1.7 ppm (s, 6H, Me), 3.1 ppm (s, 6H, Me), 3.3–3.4 ppm (t, 2H, CH$_2$), 3.9 ppm (t, 2H, CH$_2$), 7.5–7.6 ppm (m, 5H, Ph);

(10) N-$\alpha,\alpha$-dimethylbenzyl-N,N,N-triethylammonium hexafluoroantimonate, NMR: 1.7 ppm (s, 6H, Me), 2.9–3.0 ppm (t, 9H, Me), 3.3–3.4 ppm (q, 6H, CH$_2$), 7.5–7.6 ppm (m, 5H, Ph);

(11) N-$\alpha,\alpha$-dimethylbenzyl-N,N,N-trimethylammonium hexafluoroantimonate, NMR: 1.7 ppm (s, 6H, Me), 3.1 ppm (s, 9H, Me), 7.5–7.6 ppm (m, 5H, Ph);

(12) N-p-nitro-$\alpha,\alpha$-dimethylbenzyl-N,N-dimethylanilinium hexafluoroantimonate, NMR: 1.7 ppm (s, 6H, Me), 3.6 ppm (s, 6H, Me), 7.1–7.6 ppm (m, 9H, Ph);

(13) N-2-hydroxyethyl-N-p-methyl-$\alpha,\alpha$-dimethylbenzyl-N,N-dimethylammonium hexafluoroantimonate, NMR: 1.7 ppm (s, 6H, Me), 1.8 ppm (s, 3, Me), 3.1–3.2 ppm (s, 6H, Me), 3.3–3.4 ppm (t, 2H, CH$_2$), 3.9 ppm (t, 2H, CH$_2$), 7.5–7.6 ppm (m, 4H, Ph);

(14) N-2-hydroxyethyl-N-$\alpha,\alpha$-dimethylbenzyl-N,N-dimethylammonium hexafluorophosphate, NMR: 1.7 ppm (s, 6H, Me), 3.1 ppm (s, 6H, Me), 3.3–3.4 ppm (t, 2H, CH$_2$), 3.9 ppm (t, 2H, CH$_2$), 7.5–7.6 ppm (m, 5H, Ph); and

(15) N-$\alpha,\alpha$-dimethylbenzyl-N,N,N-triethylammonium tetrafluoroborate,

NMR: 1.7 ppm (s, 6H, Me), 2.9–3.0 ppm (t, 9H, Me), 3.3–3.4 ppm (q, 6H, CH$_2$), 7.5–7.6 ppm (m, 5H, Ph);

Example I-16

1-($\alpha,\alpha$-dimethylbenzyl)pyridinium hexafluoroantimonate 4.644 g (0.03 mol) of $\alpha,\alpha$-dimethylbenzyl chloride and 2.373 g (0.03 mol) of pyridine were reacted in 40 ml of methanol at 40° C. for 3 days. After the reaction, the solvent was evaporated in vacuo and ether-water was added to the residue to extract unreacted reactants in the etherial layer. To the aqueous layer was added 7.7 g (0.03 mol) of sodium hexafluoroantimonate. The resulting crystals were suction filtered, washed and dried to give the title compound.

NMR: 2.1 ppm (s, 6H, Me), 7.3-7.5 ppm (m, 5H, Ph), 8.0-8.2 ppm (t, 2H, Py), 8.5-8.8 ppm (t, 1H, Py), 9.0-9.2 ppm (d, 2H, Py)

Example I-17 to I-21

Analogous to Example I-16, the following compounds were synthesized.

(17) 1-($\alpha,\alpha$-dimethylbenzyl)-4-cyanopyridinium hexafluoroantimonate,

NMR: 2.1 ppm (s, 6H, Me), 7.3-7.5 ppm (m, 5H, Ph), 8.7 ppm (d, 2H, Py), 9.4 ppm (d, 2H, Py);

(18) 1-($\alpha,\alpha$-dimethylbenzyl)-2-chloropyridinium hexafluoroantimonate, NMR: 2.1 ppm (s, 6H, Me), 7.3-7.5 ppm (m, 5H, Ph), 8.2 ppm (t, 1H, Py), 8.4 ppm (d, 1H, Py), 8.7 ppm (t, 1H, Py), 9.3 ppm (d, 1H, Py);

(19) 1-($\alpha,\alpha$-dimethylbenzyl)-2-methylpyridinium hexafluoroantimonate, NMR: 2.1 ppm (s, 6H, Me), 2.8 ppm (s, 3H, Me), 7.3-7.5 ppm (m, 5H, Ph), 8.0-8.1 ppm (m, 2H, Py), 8.5 ppm (t, 1H, Py), 9.0 ppm (d, 1H, Py);

(20) 1-($\alpha,\alpha$-dimethylbenzyl)-3,5-dimethylpyridinium hexafluoroantimonate, NMR: 2.1 ppm (s, 6H, Me), 2.4 ppm (s, 6H, Me), 7.3-7.5 ppm (m, 5H, Ph), 8.9 ppm (m, 2H, Py), 9.4 ppm (m, 1H, Py); and

(21) 1($\alpha,\alpha$-dimethylbenzyl)-4-methylpyridinium hexafluoroantimonate,

NMR: 2.1 ppm (s, 6H, Me), 2.7 ppm (s, 3H, Me), 7.3-7.5 ppm (m, 5H, Ph), 8.1 ppm (d, 2H, Py), 90 ppm (d, 2H, Py)

Example I-22

2-phenyl-3,3-dimethyl-1,3-oxiazolidinium hexafluoroantimonate 10.6 (0.1 mol) of benzaldehyde and 7.5 g (0.1 mol) of 2-methylaminoethanol were dissolved in 5 g of benzene. The solution was refluxed until the adsorbance of OH group at 3800 cm$^{-1}$ disappeared in the IR spectrophotometry of the reaction mixture.

After the reaction, 14.2 g of methyl iodide was added dropwise at room temperature and allowed to react for 2 hours. The reaction mixture was extracted with water-ether and 25.9 g (0.1 mol) of sodium hexafluoroantimonate was added thereto. The resulting crystals were suction filtered, washed and dried to give the title compound.

NMR: 2.3 ppm (s, 3H, Me), 3.2 ppm (s, 3H, Me), 3.8-4.0 ppm (m, 2H, CH$_2$), 4.3-4.5 ppm (m, 2H, CH$_2$), 5.9 ppm (s, 1H, CH), 7.6 ppm (s, 5H, Ph)

Examples I-23 to I-28

Analogous to Example I-22, the following compounds were synthesized.

(23) 2-(4-nitrophenyl)-3,3-dimethyl-1,3-oxazolidinium hexafluoroantimonate,

NMR: 2.7 ppm (s, 3H, Me), 3.2 ppm (s, 3H, Me), 4.0 ppm (m, 2H, CH$_2$), 4,4-4,5 ppm (m, 2H, CH$_2$), 6.1 ppm (s, 1H, CH), 8.0 ppm (d, 2H, Ph), 8.4 ppm (d, 2H, Ph);

(24) 2-(2-nitrophenyl)-3,3-dimethyl-1.3-oxazolidinium hexafluoroantimonate,

NMR: 2.7 ppm (s, 3H, Me), 3.2 ppm (s, 3H, Me), 4.0 ppm (m, 2H, CH$_2$), 4,4-4,5 ppm (m, 2H, CH$_2$), 6.1 ppm (s, 1H, CH), 8.0-8.4 ppm (m, 4H, Ph);

(25) 2-(4-methoxyphenyl)-3,3-dimethyl-1,3-oxazolidinium hexafluoroantimonate,

NMR: 2.6 ppm (s, 3H, MeO), 3.1 ppm (s, 3H, Me), 3.4 ppm (s, 3H, Me), 3.9-4.1 ppm (m, 2H, CH$_2$), 4.4-4.6 ppm (m, 2H, CH$_2$), 5.9 ppm (s, 1H, CH), 7.1-7.2 ppm (d, 2H, Ph), 7.5-7.6 ppm (d, 2H, Ph);

(26) 2-(2-methoxyphenyl)-3,3-dimethyl-1,3-oxazolidinium hexafluoroantimonate,

NMR: 2.6 ppm (s, 3H, Me), 3.1 ppm (s, 3H, Me), 3.4 ppm (s, 3H, Me), 3.9-4.1 ppm (m, 2H, CH$_2$), 4.4-4.6 ppm (m, 2H, CH$_2$), 5.8 ppm (s, 1H, CH), 7.3 7.6 ppm (d, 4H, Ph);

(27) 2-t-butyl-3,3-dimethyl-1,3-oxazolidinium hexafluoroantimonate,

NMR: 1.1 ppm (s, 9H, t-Bu), 3.1 ppm (s, 3H, Me), 3.3 ppm (s, 3H, Me), 3.8 ppm (m, 2H, CH$_2$), 4.2 4.3 ppm (m, 2H, CH$_2$), 4.5 ppm (s, 1H, CH); and

(28) 2-ethyl-3,3-dimethyl-1,3-oxazolidinium hexafluoroantimonate,

NMR: 1.1 ppm (t, 3H, Me), 1.8-2.0 ppm (m, 2H, CH$_2$) 3.1 ppm (s, 3H, Me), 3.5 ppm (s, 3H, Me), 3.8 ppm (m, 2H, CH$_2$), 4.2-4.3 ppm (m, 2H, CH$_2$), 4.6-4.7 ppm (m, 1H, CH)

Part II. Production of Vehicle Resins

Polyester Resin

Example II-1

A reaction vessel provided with a heater, stirrer, reflux condenser, water separator, fractional distillation column and thermometer was charged with 36 parts of hexahydrophthalic acid, 42 parts of trimethylolpropane, 50 parts of neopentyl glycol and 56 parts of 1,6-hexanediol. The mixture was heated to 210° C. with stirring. Then the mixture was heated to 230° C. at a constant rate over 2 hours while distilling out water formed as a by-product by the condensation reaction. The rection was continued at 230° C. until an acid number of 1.0 was reached and stopped by cooling. After the addition of 153 parts of isophthalic acid, the reaction mixture was heated again to 190° C. and thereafter form 190° C. to 210° C. at a constant rate over 3 hours while distilling out formed water. When this temperatue was reached, 3 parts of xylene was added and the rection was continued until an acid number of 5.0 was reached. After cooling, the rection mixture was diluted with 190 parts of xylene whereupon Polyester Resin A was obtained.

Acrylic Resin

Example II-2

A reaction vessel provided with a stirrer, thermometer, reflux condenser, nitrogen gas-introducing tube and dripping funnel was charged with 90 parts of SOLVESSO 100 and heated to 160° C. while introducing nitrogen gas. To the vessel was added dropwise the following monomer mixture at a constant rate:

| | |
|---|---|
| 2-Hydroxyethyl methacrylate | 23.20 Parts |
| Methyl methacrylate | 40.15 Parts |
| n-Butyl acrylate | 35.65 Parts |
| Methacrylic acid | 1.00 Parts |
| t-Butylperoxy-2-ethylhexanoate | 10.00 Parts |

One hour after the addition, a mixture of 10 parts of xylene and 1 part of t-butylperoxy-2-ethylhexanoate was added dropwise at a constant rate over 30 minutes.

The reaction was allowed to proceed to completion for 2 hours and stopped by cooling to give Acrylic Resin A.

Example II-3

A reaction vessel provided with a stirrer, thermometer, reflux condenser, nitrogen gas-introducing tube and dripping funnel was charged with 90 parts of SOLVESO 100 and heated to 120° C. while introducing nitrogen gas. To the vessel was added dropwise the following monomer mixture at a constant rate:

| | |
|---|---|
| Methyl methacrylate | 28.11 parts |
| Styrene | 25.00 parts |
| Glycidyl methacrylate | 30.00 parts |
| n-Butyl acrylate | 2.59 parts |
| Isobutyl methacrylate | 1.88 parts |
| t-Butylperoxy-2-ethylhexanoate | 5.00 parts |

One hour after the addition, a mixture of 10 parts of xylene and 1 part of t-butylperoxy-2-ethylhexanoate as added dropwise at a constant rate over 30 minutes. The reaction was allowed to proceed to completion for 2 hours and stopped by cooling to give Acrylic Resin B.

Example II-4

A reaction vessel provided with a stirrer, thermometer, reflux condenser, nitrogen gas-introducing tube and dripping funnel was charged with 90 parts of SOLVESSO 100 and heated to 120° C. while introducing nitrogen gas. To the vessel was added dropwise the following monomer mixture at a constant rate:

| | |
|---|---|
| Methyl methacrylate | 23.11 Parts |
| Styrene | 30.00 Parts |
| Glycidyl methacrylate | 25.00 parts |
| n-Butyl acrylate | 2.59 parts |
| Isobutyl methacrylate | 1.00 parts |
| 2-Hydroxyethyl methacrylate | 12.42 parts |
| t-Butylperoxy-2-ethylhexanoate | 5.00 parts |

One hour after the addition, a mixture of 10 parts of xylene and 1 part of t-butylperoxy-2-ethylhexanoate was added dropwise at a constant rate over 30 minutes. The reaction was allowed to proceed to completion for 2 hours and stopped by cooling to give Acrylic Resin C.

Silicon Resins

Example II-5

A reaction vessed used in Example II-2 was charged with 45 parts of xylene and heated to 130° C. while introducing nitrogen gas. To the vessel was added dropwise a mixture of 50 parts of γ-methacryloyloxypropyltrimethoxysilane and 4 parts of t-butylperoxy-2-ethylhexanoate at a constant rate over 3 hours.

30 minutes after the addition, the mixture was cooled to 90° C., and a mixture of 1 part of t-butylperoxy-2-ethylhexanoate and 5 parts of xylene was added thereto. The reaction was allowed to proceed to completion for additional 2 hours and stopped by cooling to give Silicon Resin A.

Example II-6

Analogous to Example II-5, a mixture of 50 parts of γ-methacryloyloxypropylmethyldimethoxysilane and 4 parts of t-butylperoxy-2-ethylhexanoate was polymerized to give Silicon Resin B.

Example II-7

Analogous to Example II-5, a mixture of 50 parts of γ-methacryloyloxypropyldimethylmethoxysilane and 4 parts of t-butylperoxy-2-ethylhexanoate was polymerized to give Silicon Resin C.

Example II-8

Analogous to Example II-5, a mixture of 50 parts of γ-methacryloyloxypropyltriethoxysilane and 4 parts of t-butylperoxy-2-ethylhexanoate was polymerized to give Silicon Resin D.

Example II-9

Analogous to Example II-5, a mixture of 25 parts of γ-methacryloyloxypropyltriethoxysilane, 25 parts of methyl methacrylate and 4 parts of t-butylperoxy-2-ethylhexanoate was polymerized to give Silicon Resin E.

Example II-10

A reaction vessel provided with a stirrer, thermometer and reflux condenser was charged with 100 parts of Polyester Resin A obtained in Example II-1 and heated to 100° C. After the addition of 0.2 parts of dibutyltin dilaurate, 10 parts of KBK-9007 (chemically γ-isocyanatopropyltrimethoxysilane sold by Shin-Etsu Chemical Co., Ltd.) were added dropwise at a constant rate over 30 minutes and the reaction allowed to proceed to completion for additional 1 hour. After cooling, Silicon Resin F was obtained. The absorption of NCO group at 1720 cm$^{-1}$ disappeared completely in the IR spectrometry of the resin.

Example II-11

A reaction vessel provided with a stirrer, thermometer and reflux condenser was charged with 100 parts of bisphenol A diglycidyl ether and heated to 150° C. The 100 parts of γ-aminopropyltrimethoxy-silane were added dropwise at a constant rate over 1 hour and allowed to react for additional 1 hour. After cooling, Silicon Resin G was obtained. Part II. Cation Polymerization System

Example II-1

90 parts on solid basis of Acrylic Resin B were mixed with 2 parts of 1-(α,α-dimethylbenzylpyridinium hexafluoroantimonate. The mixture was cast on a tinplate and baked at 120° C. The storage stability and curability of the mixture were tested. The test conditions and results are shown in Table III.

Example III-2

The procedure of Example III-1 was repeated using a mixture of 90 parts on solid basis of Acrylic Resin B and 2 parts of N-(α,α-dimethylbenzyl)-N,N-dimethylanilinium hexafluoroantimonate.

Example III-3

The procedure of Example III-1 was repeated using a mixture of 90 parts on solid basis of Acrylic Resin C and 2 parts of N-(4-chloro-α,α-dimethylbenzyl)-pyridinium hexafluoroantimonate.

Example III-4

The procedure of Example III-1 was repeated using a mixture of 90 parts on solid basis of Acrylic Resin B and 2 parts of N-α-methylbenzylpyridinium hexafluoroantimonate.

Example III-5

The procedure of Example III-1 was repeated using a mixture of 90 parts on solid basis of Acrylic Resin C and 2 parts of 2-phenyl-3,3-dimethyl-1,3-oxazolidinium hexafluoroantimonate.

Example III-6

The procedure of Example III-1 was repeated using a mixture of 90 parts on solid basis of Acrylic Resin C and 1 part of 2-(4-methylphenyl)-3,3-dimethyl-1,3-oxazolidinium hexafluoroantimonate.

Example III-7

The procedure of Example III-1 was repeated using a mixture of 90 parts on solid basis on Acrylic Resin C and 2 parts of N-(α,α-dimethylbenzyl)-N,N-dimethylanilinium hexafluoroantimonate.

Example III-8

The procedure of Example III-1 was repeated using a mixture of 90 parts on solid basis of Acrylic Resin C and 2 parts of 2-(2-methylphenyl)-3-methyl-3-ethyl-1,3-oxazolidinium hexafluoroantimonate.

Example III-9

The procedure of Example III-1 was repeated using a mixture of 100 parts of ERL-4206 (alicyclic epoxy resin sold by UCC) and 0.5 parts of N-(α,α-dimethylbenzyl)-pyridinium hexafluoroantimonate.

Example III-10

The procedure of Example III-1 was repeated using a mixture of 100 parts of Epikote 1001 (epoxy resin sold by Shell Chemical) and 0.5 parts of 2-(4-methylphenyl)-3,3-dimethyl-1,3-oxazolidinium hexafluoroanatimonate.

Example III-11

The procedure of Example III-1 was repeated using a mixture of 90 parts of Acrylic Resin C, 10 parts of ERL-4206 and 0.5 parts of N-(α,α-dimethylbenzyl)-pyridinium hexafluoroantimonate.

Example III-12

The procedure of Example III-1 was repeated using a mixture of 70 parts of Acrylic Resin C, 30 parts of ERL-4206 and 0.5 parts of 2-(4-methypheny)-3,3-dimethyl-1,3-oxazolidinium hexafluoroantimonate.

(trifunctional polycaprolactone polyol of M.W. of 860 sold by Daicel Chemical Industries, Ltd.). The mixture was cast on a tinplate and baked at 130° C. for 30 minutes.

The curability and storagte stability of the mixture as Shown in Table IV.

Example IV-2

The procedure of Example IV-1 was repeated using a mixture of 100 parts of Acrylic Resin B, 0.5 parts of N-(α-methylbenzyl)-N,N-dimethylanilinium hexafluoroantimonate and 5 parts of 1,6-hexanediol.

Example IV-3

The procedure of Example IV-1 was repeated using 100 parts of Acrylic Resin B, 0.5 parts of 2-(4-methylphenyl)-3,3-dimethyl-1,3-oxazolidinium hexafluoroantimonate and 5 parts of polyesther polyol (trifunctional, M.W. 800).

TABLE IV

|  | Example | | |
|---|---|---|---|
|  | IV-1 | IV-2 | IV-3 |
| Curability[1] | ⊚ | ⊚ | ○ |
| Storage Stability[2] | ○ | ○ | ⊚ |

[1] Film appearance after the MEK rubbing test (100 reciprocations). ⊚: No change; ○: Slightly dissolved; Δ: Whitening; x: Dissolved
[2] Viscosity increase after storing in a closed system at 40° C. for 2 weeks. ⊚: No increase; ○: Slightly increased; Δ: Increased; x: Gelling

Part V. Systems Containing Melamine Resins

Example V-1

70 parts of PLACCEL 308, parts of CYMEL 303 (melamine resin sold by Mitui Toatsu Chemicals, Inc.) and 2 parts of N-(α-methylbenzyl)-N,N-bis(hydroxyethyl)-ammonium hexafluoroantimonate were thoroughly mixed. The mixture as cast on a tinplate and baked at 140° C. The curability and storage stability of the mixture are shown in Table V.

Example V-2

The procedure of Example V-1 was repeated using a mixture of 70 parts of PLACCEL 308, 30 parts of CYMEL 303 and 2 parts of 2-phenyl-3,3-dimethyl-1,3-oxazolidinium hexafluorotntimonate.

Example V-3

The procedure of Example V-1 was repeated using a mixture of 50 parts of PLACCEL 308, 50 parts of CYMEL 303 and 2 parts of 2-phenyl-3,3-dimethyl-1,3-oxazolidinium hexafluorophosphate.

Example V-4

The procedure of Example V-1 was repeated using 90 parts on solid basis of polyester Resin A, 10 parts of

TABLE III-1

|  | Example | | | | | | | | | | | |
|---|---|---|---|---|---|---|---|---|---|---|---|---|
|  | III-1 | III-2 | III-3 | III-4 | III-5 | III-6 | III-7 | III-8 | III-9 | III-10 | III-11 | III-12 |
| Curability[1] | ○ | ○ | ⊚ | ○ | ⊚ | ⊚ | ⊚ | ⊚ | ⊚ | ○ | ⊚ | ○ |
| Storage Stability[2] | ⊚ | ⊚ | ○ | ⊚ | ○ | ⊚ | ⊚ | ○ | ○ | ⊚ | ○ | ⊚ |

[1] Film appearance after the MEK rubbing test (100 reciprocations). ⊚: No change; ○: Slightly dissolved; Δ: Whitening; x: Dissolved
[2] Viscosity increase after storing in a closed system at 40° C. for 2 weeks. ⊚: No increase; ○: Slightly increased; Δ: Increased; x: Gelling

Part IV. Cation Polymerization System Containing Polyols

Example IV-1

100 parts of Acrylic Resin B were thoroughly mixed with 0.5 parts of N-(α,α-dimethylbenzyl)pyridinium hexafluoroantimonate and 2.95 parts of PLACCEL 308

CYMEL 303 and 2 parts of N-(α,α-dimethylbenzyl)-pyridinium hexafluorophosphate.

Example V-5

The procedure of Example V-1 was repeated using a mixture of 60 parts on solid basis of polyester Resin A, 40 parts of solid basis of YUBAN 20SE (melamine resin sold by Mistui Toatsu Chemicals, Inc.) and 2 parts of N-(α,α-dimethylbenzyl)pyridinium tetrafluoroborate.

Example V-6

The procedure of Example V-1 was repeated using a mixture of 70 parts on solid basis of Polyester Resin A, 30 parts on solid basis of Yuban 20SE and 2 parts of 2-(4-methylphenyl)-3,3-dimethyl-1,3-oxazolidinium tetrafluoroborate.

Example V-7

The procedure of Example V-1 was repeated using a mixture of 90 parts on solid basis of Acrylic Resin A, 10 parts of CYMEL 303 and 2 parts of 2-(4-methoxyphenyl)-3,3-dimethyl-1,3-oxazolidinium hexafluoroantimonate.

Example V-8

The procedure of Example V-1 was repeated using a mixture of 60 parts on solid basis of Acrylic Resin A, 40 parts on solid basis of YUBAN 20SE and 2 parts of N-(4-chloro-α-methylbenzyl)-pyridinium hexafluorophosphate.

Example V-9

The procedure of Example V-1 was repeated using a mixture of 70 parts on solid basis of Acrylic Resin A, 30 parts on solid basis of YUBAN 20SE and 2 partds of N-(α-methylbenzyl)-N,N-dimethyl-N-2-hydroxyethylammonium hexafluorophosphate.

Example VI-2

The procedure of Example VI-1 was repeated using a mixture of 100 parts of Acrylic Resin A, 29.9 parts of Silicon Resin B, 5 parts of methanol and 2.58 parts of 2-(4-methoxyphenyl)-3,3-dimethyl-1,3-oxazolidinium hexafluoroantimonate.

Example VI-3

The procedure of Example VI-1 was repeated using a mixture of 100 parts of Acrylic Resin A, 26.9 parts of Silicon Resin C, 5 parts of methanol and 2.54 parts of 2-phenyl-3,3-dimethyl-1,3-oxazolidinium hexafluoroantimonate.

Example VI-4

The procedure of Example VI-1 was repeated using a mixture of 100 parts of Acrylic Resin A, 36.2 parts of Silicon Resin D, 5 parts of methanol and 2.72 parts of 2-(2-methylphenyl)-3,3-dimethyl-1,3-oxazolidinium hexafluorophosphate.

Example VI-5

The procedure of Example VI-1 was repeated using a mixture of 100 parts of Acrylic Resin A, 43.4 parts of Silicon Resin E, 5 parts of methanol and 2.87 parts of N-(α-methylbenzyl)-N,N-dimethyl-N-2-hydroxyethylammonium hexafluorophosphate.

Example VI-6

The procedure of Example VI-1 was repeated using a mixture of 100 parts of Polyester Resin A, 30 parts of Silicon Resin F, 5 parts of methanol and 2.87 part of N-(α,α-dimethylbenzyl)pyridinium hexafluorophosphate.

Example VI-7

The procedure of Example VI-1 was repeated using a mixture of 100 parts of Polyester Resin A, 18 parts of Silicon Resin G, 5 parts of methanol and 2.87 parts of N-(α-methylbenzyl)-N,N-dimethylanilinium hexafluoroantimonate.

TABLE V

| | Example | | | | | | | | |
|---|---|---|---|---|---|---|---|---|---|
| | V-1 | V-2 | V-3 | V-4 | V-5 | V-6 | V-7 | V-8 | V-9 |
| Curability[1] | ⊙ | ○ | ○ | ○ | ⊙ | ○ | ⊙ | ○ | ⊙ |
| Storage Stability[2] | ○ | ⊙ | ⊙ | ⊙ | ○ | ⊙ | ⊙ | ⊙ | ○ |

[1] Film appearance after the MEK rubbing test (100 reciprocations). ⊙: No change; ○: Slightly changed; Δ: Whitening; x: Dissolved
[2] Viscosity increase after storing in a closed system at 40° C. for 2 weeks. ⊙: No increase; ○: Slightly increased; Δ: Increased; x: Gelling

Part VI. Alkoxysilyl Group Self- and Co-Condensation Systems

Example VI-1

100 parts of Acrylic Resin A, 30.9 parts of Silicon Resin A, 5 parts of methanol and 2.62 parts of N-(α,α-dimethylbenzyl)-pyridinium hexafluoroantimonate were thoroghly mixed. The mixture was cast on a steel plate, allowed to set for 2 hours and baked at 140° C. for 30 minutes. The curability and storage stability of the mixture are shown in Table VI.

Example VI-8

The procedure of Example VI-1 was repeated using a mixture of 100 parts of Silicon Resin B, 5 parts of methanol and 2.58 parts of N-(α-methylbenzyl)-N,N-dimethyl-N-(o-tolyl)ammonium hexafluoroantimonate.

Example VI-9

The procedure of Example VI-1 was repeated using a mixture of 100 parts of Acrylic Resin A, 10.3 parts of Silicon Resin A, 20.6 parts of CYMEL 303, 5 parts of methanol and 2.62 parts of N-(α,α-dimethylbenzyl)-pyridinium tetrafluoroborate.

TABLE VI

| | Example | | | | | | | | |
|---|---|---|---|---|---|---|---|---|---|
| | VI-1 | VI-2 | VI-3 | VI-4 | VI-5 | VI-6 | VI-7 | VI-8 | VI-9 |
| Curability[1] | ⊙ | ⊙ | ⊙ | ⊙ | ⊙ | ⊙ | ⊙ | ⊙ | ⊙ |
| Storage | ○ | ○ | ○ | ○ | ○ | ○ | ○ | ○ | ○ |

TABLE VI-continued

|  | Example | | | | | | | | |
|---|---|---|---|---|---|---|---|---|---|
|  | VI-1 | VI-2 | VI-3 | VI-4 | VI-5 | VI-6 | VI-7 | VI-8 | VI-9 |
| Stability[2] | | | | | | | | | |

[1] Film appearance after the MEK rubbing test (100 reciprocations). ⊙: No change; ○: Slightly changed; Δ: Whitening; x: Dissolved

[2] Viscosity increase after storing in a closed system at 40° C. for 2 weeks. ⊙: No change; ○: Slightly increased; Δ: Increased; x: Gelling

We claim:

1. A resinous composition comprising a film-forming resin capable of curing upon heating in the presence of a curing catalyst and an amount effective to initiate the curing reaction of said resin of a compound of the formula:

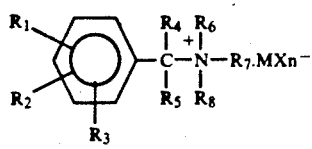

wherein $R_1$, $R_2$ and $R_3$ are each hydrogen, halogen, alkyl, alkoxy, nitro, amino, alkylamino, cyano, alkoxycarbonyl or carbamoyl; $R_4$ is hydrogen, halogen or alkyl; $R_5$ is halogen or alkyl; $R_6$, $R_7$ and $R_8$ are each alkyl or alkenyl optionally substituted with hydroxy, carboxyl, alkoxy, nitro, cyano or alkanoyloxy, or phenyl optionally substituted with alkyl, halogen, nitro, cyano, alkoxy, amino or dialkylamino; M is As, Sb, B or P; X is halogen; and n equals the valency of the element M plus one; or

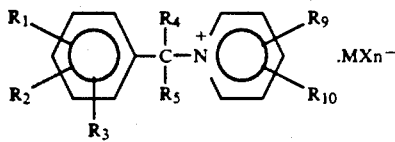

wherein $R_1$, $R_2$, $R_3$, $R_4$, $R_5$, M, X and n are as defined above with proviso that $R_4$ cannot represent hydrogen; $R_9$ and $R_{10}$ are each hydrogen, alkyl, halogen, nitro, cyano, alkoxy, amino or dialkylamino; or

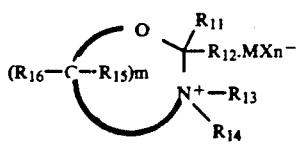

wherein M, X and n are as defined above; $R_{11}$ and $R_{12}$ are each hydrogen, alkyl, alkenyl or phenyl optionally substituted with hydroxy, alkyl, alkoxy, halogen, nitro, cyano or alkylamino; $R_{13}$ and $R_{14}$ are each alkyl, alkenyl or phenyl optionally substituted with hydroxy, alkyl, alkoxy, halogen, nitro, cyano or alkylamino; $R_{15}$ and $R_{16}$ are each hydrogen, hydroxy, alkyl, alkoxy or phenyl optionally substituted with hydroxy, alkyl, alkoxy, halogen, nitro, cyano or alkylamino; and m is an integer of 1-4.

2. The resinous composition according to claim 1, wherein said film-forming resin is a monomer or polymer having a cation polymerizable function, or a mixture thereof.

3. The resinous composition according to claim 2, wherein said cation polymerizable function is a cyclic imine, cyclic ether or cyclic ester.

4. The resinous composition according to claim 2, wherein said film-forming resin further contains a polyol.

5. The resinous composition according to claim 4, said polyol component is compounded in an amount corresponding to 1 to 100 mole % relative to said cation polymerizable function.

6. The resinous composition according to claim 1, wherein said film-forming resin is a mixture of a film-forming resin having a plurality of hydroxy groups and a melamine resin.

7. The resinous composition according to claim 6, wherein said melamine resin occupies from 5 to 50% of the solid content of said mixture.

8. The resinous composition according to claim 1, wherein said film-forming resin is a silicon resin having a plurality of alkoxysilyl groups.

9. The resinous composition according to claim 8 further comprising a polyol.

10. The resinous composition according to claim 9, wherein said polyol component is compounded in such an amount that the molar ratio of the hydroxy group to the alkoxysilyl group is 0.1 to 10.

11. The resinous composition according to claim 1, wherein said film-forming resin further contains a polyol, in an amount corresponding to 1 to 100 mole % relative to said cation polymerizable function.

* * * * *